(12) United States Patent
Wu et al.

(10) Patent No.: US 9,414,878 B1
(45) Date of Patent: Aug. 16, 2016

(54) CRYOGENIC BALLOON ABLATION SYSTEM

(71) Applicant: C2 Therapeutics, Inc., Redwood City, CA (US)

(72) Inventors: Patrick P. Wu, San Carlos, CA (US); Timothy Douglas Holland, Los Gatos, CA (US); Cesar A. Ico, San Francisco, CA (US); Richard S. Williams, Redwood City, CA (US); Gabriel Francis W. Newell, San Francisco, CA (US)

(73) Assignee: C2 Therapeutics, Inc., Redwood City, CA (US)

( * ) Notice: Subject to any disclaimer, the term of this patent is extended or adjusted under 35 U.S.C. 154(b) by 0 days.

(21) Appl. No.: 14/714,101

(22) Filed: May 15, 2015

(51) Int. Cl.
*A61B 18/02* (2006.01)
*A61B 19/00* (2006.01)
*A61B 18/00* (2006.01)

(52) U.S. Cl.
CPC ........... *A61B 18/02* (2013.01); *A61B 19/44* (2013.01); *A61B 2018/0022* (2013.01); *A61B 2018/00196* (2013.01); *A61B 2018/00488* (2013.01); *A61B 2018/00577* (2013.01); *A61B 2018/00744* (2013.01); *A61B 2018/0212* (2013.01); *A61B 2018/0262* (2013.01); *A61B 2019/448* (2013.01)

(58) Field of Classification Search
CPC ........... A61B 18/02; A61B 2018/0022; A61B 2018/0212; A61B 2018/0262; A61B 2018/0268
USPC ......................... 606/20–23, 25, 26
See application file for complete search history.

(56) References Cited

U.S. PATENT DOCUMENTS

| 5,035,705 | A | 7/1991 | Burns |
| 5,342,301 | A | 8/1994 | Saab |
| 5,971,979 | A | 10/1999 | Joye et al. |
| 6,355,029 | B1 * | 3/2002 | Joye ............. A61B 18/02 606/21 |
| 6,443,947 | B1 | 9/2002 | Marko et al. |
| 6,537,271 | B1 | 3/2003 | Murray et al. |
| 6,875,209 | B2 | 4/2005 | Zvuloni et al. |
| 7,220,257 | B1 | 5/2007 | Lafontaine |
| 7,727,228 | B2 | 6/2010 | Abboud et al. |
| 8,382,746 | B2 | 2/2013 | Williams et al. |

(Continued)

FOREIGN PATENT DOCUMENTS

WO 9927862 A1 6/1999

OTHER PUBLICATIONS

International Search Report and Written Opinion from corresponding PCT application No. PCT/US2014/063518; Feb. 9, 2015; 15 pgs.

*Primary Examiner* — Michael Peffley
*Assistant Examiner* — Thomas Giuliani
(74) *Attorney, Agent, or Firm* — James F. Hann; Haynes Beffel & Wolfeld LLP

(57) ABSTRACT

A cryogenic ablation catheter includes a catheter shaft, a balloon and a connector respectively at the catheter shaft proximal and distal ends, a refrigerant delivery tube assembly including a refrigerant delivery tube translatable within the catheter shaft lumen, and a refrigerant delivery element with an outlet located inside the balloon which directs refrigerant outwardly against the balloon at different axial positions as it translates. A cryogenic balloon ablation system includes the cryogenic ablation catheter, a catheter coupler mating with the connector, a linear motion assembly, and a connection line fluidly coupled to a refrigerant fluid source for supplying refrigerant fluid to the refrigerant delivery tube.

11 Claims, 10 Drawing Sheets

(56) References Cited

U.S. PATENT DOCUMENTS

| | | |
|---|---|---|
| 8,409,266 B2 | 4/2013 | Lafontaine |
| 9,050,073 B2 | 6/2015 | Newell et al. |
| 2002/0010460 A1 | 1/2002 | Joye et al. |
| 2002/0026182 A1* | 2/2002 | Joye ................ A61B 18/02 606/21 |
| 2002/0062122 A1 | 5/2002 | Lehmann et al. |
| 2003/0088240 A1 | 5/2003 | Saadat |
| 2007/0299443 A1 | 12/2007 | DiPoto et al. |
| 2009/0118723 A1 | 5/2009 | Lalonde et al. |
| 2009/0182317 A1* | 7/2009 | Bencini ............ A61B 18/02 606/21 |
| 2009/0209949 A1 | 8/2009 | Ingle et al. |
| 2009/0234345 A1 | 9/2009 | Hon |
| 2010/0130970 A1 | 5/2010 | Williams et al. |
| 2010/0249601 A1 | 9/2010 | Courtney |
| 2011/0184398 A1* | 7/2011 | Desrochers ........ A61B 18/02 606/21 |
| 2012/0130458 A1 | 5/2012 | Ryba et al. |
| 2012/0143177 A1 | 6/2012 | Avitall |
| 2012/0197245 A1 | 8/2012 | Burnett et al. |
| 2013/0012772 A1* | 1/2013 | Gunday .......... A61B 17/22012 600/104 |
| 2013/0018366 A1 | 1/2013 | Wu et al. |
| 2013/0023770 A1 | 1/2013 | Courtney et al. |
| 2013/0110100 A1 | 5/2013 | Groves et al. |
| 2013/0231650 A1* | 9/2013 | Watson ............ A61M 25/1006 606/20 |
| 2013/0253491 A1* | 9/2013 | Burr ................ A61B 18/0218 606/21 |
| 2013/0289549 A1* | 10/2013 | Nash ................ A61B 18/02 606/21 |
| 2013/0345688 A1 | 12/2013 | Babkin et al. |

* cited by examiner

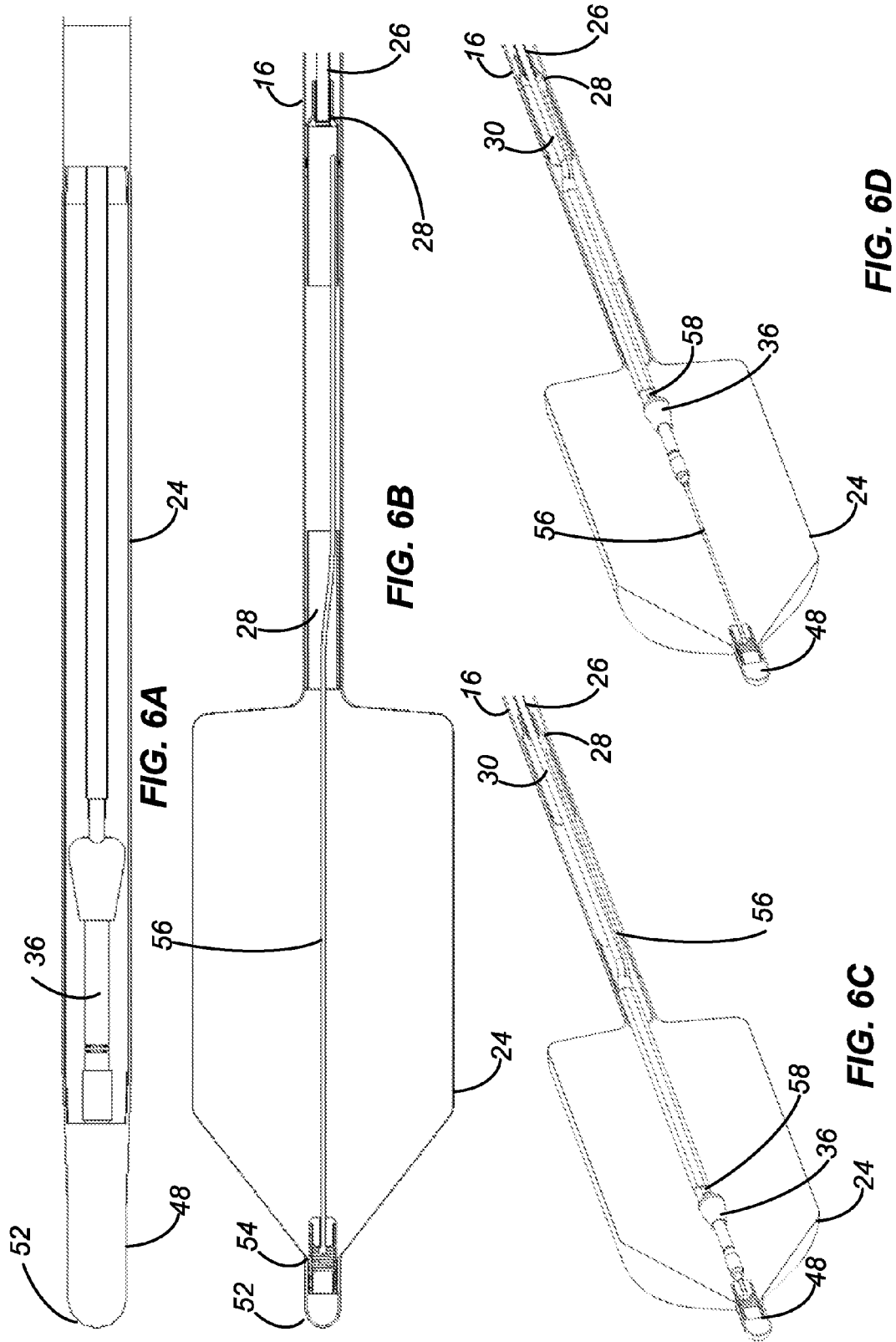

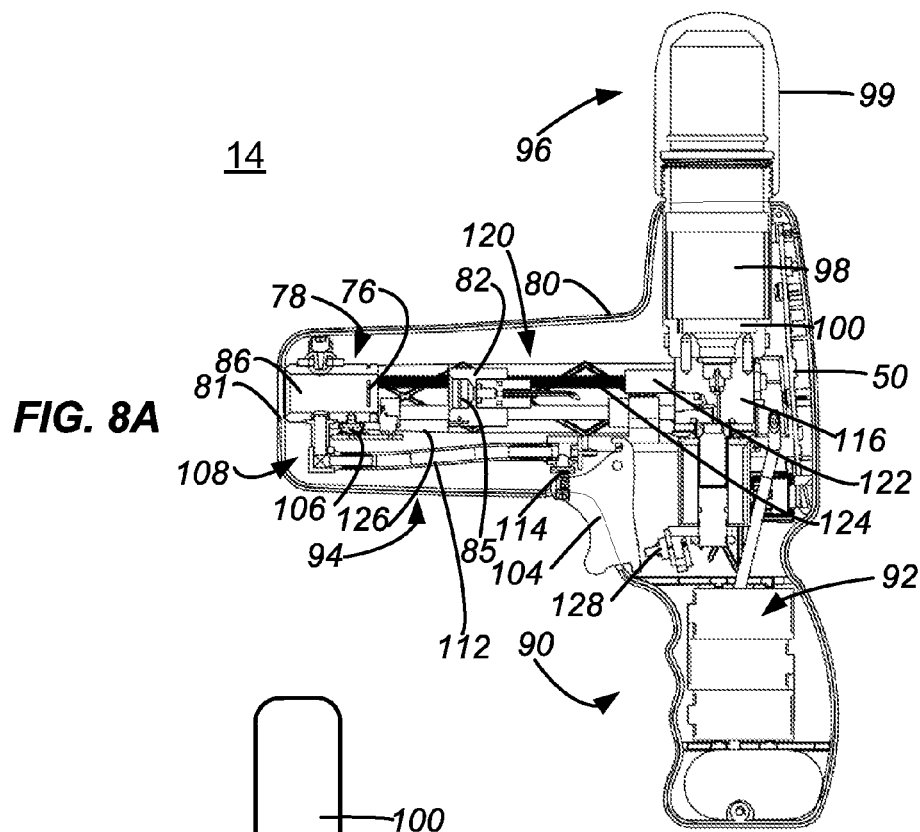
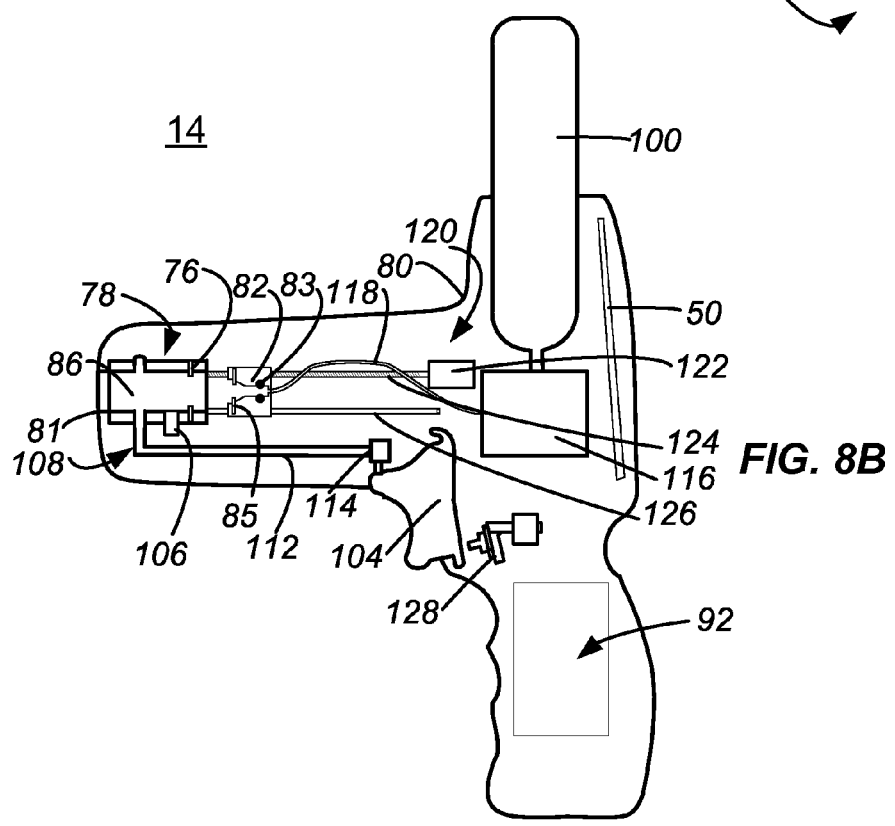

CRYOGENIC BALLOON ABLATION SYSTEM

BACKGROUND

Throughout the human body there are lumens, such as the esophagus and colon, which may have components which may become metaplastic or neoplastic. Often, it is desirable to remove or destroy these unwanted tissues. One of these cases where tissue removal and/or ablation are desirable is Barrett's Esophagus, which is a pre-cancerous condition of the esophagus typically often associated with gastric reflux disease (GERD). Although GERD can be medically controlled, Barrett's Esophagus does not spontaneous resolve once the GERD has abated. However, it has been shown that if Barrett's Esophagus is ablated, the normal esophagus lining can be restored and therefore lower the risk of developing esophageal cancer.

A variety of techniques have been evaluated for ablation of this condition. These techniques include cryogenic ablation via a direct spray of liquid nitrogen. One challenge in treating these types of lesions with cryogenic ablation relates to delivery sufficient refrigerant for ablation over a large lesion area.

BRIEF SUMMARY OF THE INVENTION

An Embodiment of a cryogenic ablation catheter includes a catheter shaft, an expandable and collapsible balloon, a connector, and a refrigerant delivery tube assembly. The catheter shaft has proximal and distal ends and a catheter shaft lumen extending between the ends. The balloon is mounted to the distal end of the catheter shaft and has an inner surface defining a balloon interior. The connector is at the proximal end of the catheter shaft. Within the catheter shaft is a pressure detecting tube extending from the connector to a position toward the distal end of the catheter shaft. The refrigerant delivery tube assembly includes a delivery tube, a plug and a diffuser. A portion of the delivery tube is located within the lumen of the pressure detecting tube and is configured for axial movement relative to the length of the pressure detecting tube. A first end of the delivery tube is affixed to the plug and the second end is affixed to the diffuser. Axial movement of the delivery tube causes the diffuser to translate between a position proximate to the distal end of the catheter shaft and a position proximate to the distal end of the balloon. The movement of the diffuser is constrained by a rail with a first end affixed to a flexible tip of the balloon and a second end located within the catheter shaft. The diffuser may be configured to direct refrigerant radially outwardly towards the surface of the balloon interior. During treatment, refrigerant may be delivered outwardly toward the surface of the balloon interior during translation of the diffuser. This translation causes refrigerant to be delivered to a larger portion of the balloon interior than a stationary diffuser with the same flow rate of refrigerant.

The cryogenic ablation catheter is connected to a handle assembly by engaging the connector with a connector coupler affixed to housing of the handle assembly, and the plug with a plug coupler in the handle assembly. The plug coupler is configured to translate position within the handle assembly relative to the connector coupler. This translation of the plug coupler causes translation of the delivery tube assembly. A linear motion assembly is connected to the plug coupler. In embodiments the linear motion assembly includes a motor and a lead screw configured for translation of the plug coupler within the housing.

The pressure detecting tube, within the catheter shaft, has a distal end fluidly coupled to a pressure detecting passage in the connector. The pressure detecting passage is fluidly coupled to a pressure transducer in the handle assembly. The catheter shaft and the pressure detecting tube are affixed to the connector so the proximal end of the pressure detecting tube and catheter shaft are concentric. Near the distal end of the catheter shaft a bracket is fixed to the inner wall of the catheter shaft and outer wall of the pressure detecting tube. This bracket positions the distal end of the pressuring detecting tube concentric to the catheter shaft. The cavity formed between the outer wall of the pressure detecting tube and inner wall of the catheter shaft forms an exhaust lumen. The bracket is configured to have a minimal effect on the cross-sectional area of the exhaust lumen. The exhaust lumen allows exhaust gas to be vented from the balloon interior, through the connecter, out an exhaust assembly in the handle assembly. The exhaust assembly includes at least one user controlled exhaust valve which may be actuated mechanically or electrically with an actuator. The exhaust assembly further includes a pressure relief valve configured to open if the pressure within the pressure detecting lumen is above a hold pressure.

The handle assembly further includes a refrigerant fluid source, a flow control valve (for example a solenoid valve), a connection line, and a controller. The controller may be used to control the delivery of refrigerant and translation of the delivery tube assembly. The controller includes circuitry connected to the flow control valve and linear motion assembly. When a user initiates a treatment, the controller may signal the flow control valve to begin a flow of refrigerant from the source. The refrigerant flows from the refrigerant fluid source through the flow control valve, through the connection line, through a passage in the plug coupler, through the plug and into the delivery tube. The connection line is configured to have a shape that allows the connection line to be flexed and unflexed during translation of the plug coupler while maintaining a consistent fluid passage for refrigerant.

In embodiments, the controller further includes circuitry to receive inputs that allow determination of axial position of the delivery tube assembly, speed of translation, pressure of the balloon, flow rate of the refrigerant, specifications of the catheter assembly. A combination of input values may be used in a treatment algorithm to determine the control of the flow control valve and linear motor assembly.

Other features, aspects and advantages of the present invention can be seen on review the drawings, the detailed description, and the claims which follow.

BRIEF DESCRIPTION OF THE DRAWINGS

FIG. 6A is a detailed view of the balloon of FIG. 2A.

FIG. 6B is a detailed cross section view of the balloon of FIG. 2B with the delivery tube and diffuser omitted for clarity.

FIG. 6C is a detailed cross section view of the balloon of FIG. 2B

FIG. 6D is a detailed cross section view of the balloon of FIG. 2C

FIG. 8A is a cross section view of the handle assembly.

FIG. 8B is a simplified schematic cross section corresponding to FIG. 8A.

DESCRIPTION OF INVENTION

Figure 1:
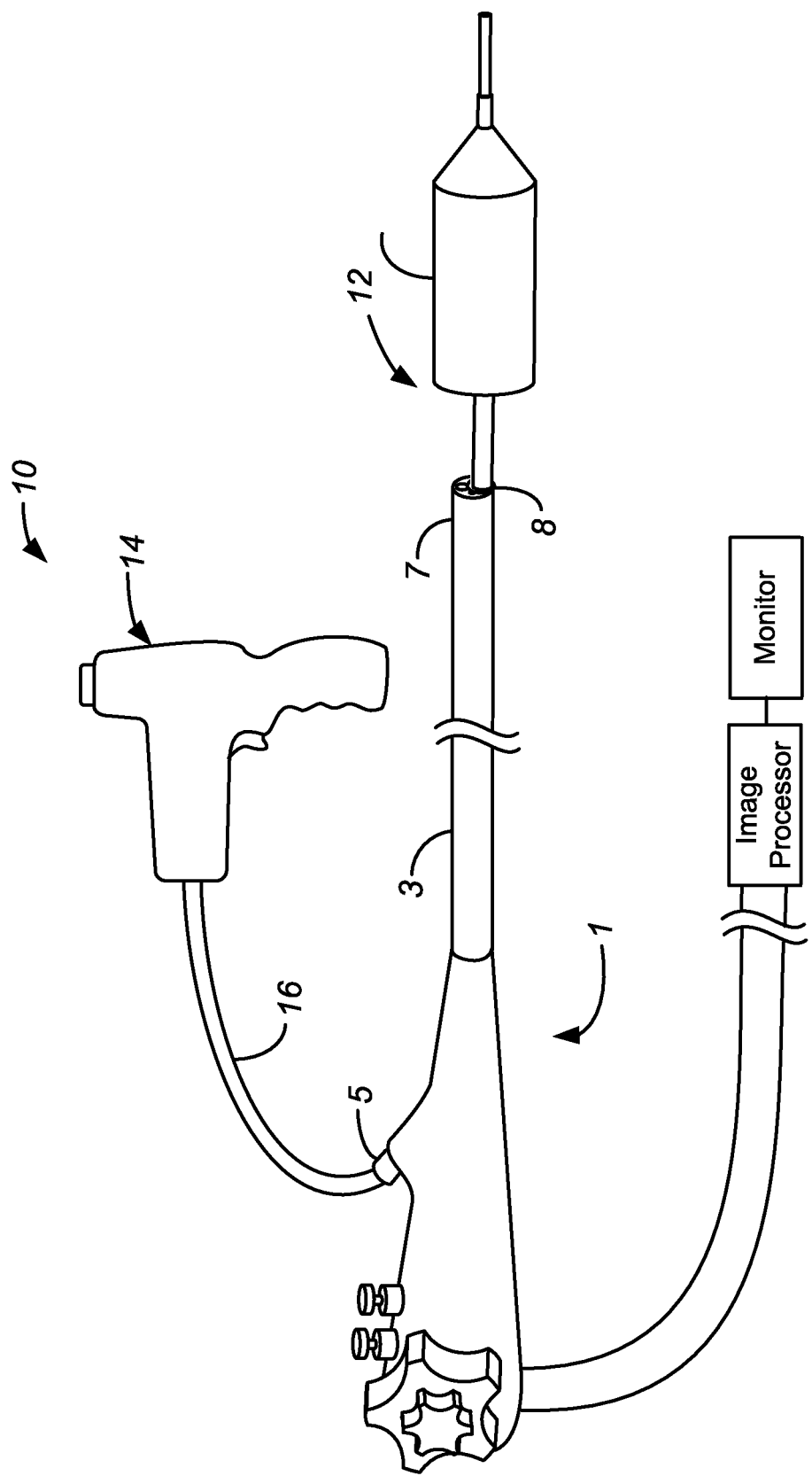
FIG. 1 is a simplified schematic overall view of an example of an ablation system including a cryogenic balloon ablation assembly and an endoscope.

The following description will typically be with reference to specific structural embodiments and methods. It is to be understood that there is no intention to limit the invention to the specifically disclosed embodiments and methods but that the invention may be practiced using other features, elements, methods and embodiments. Preferred embodiments are described to illustrate the present invention, not to limit its scope, which is defined by the claims. Those of ordinary skill in the art will recognize a variety of equivalent variations on the description that follows. Unless otherwise stated, in this application specified relationships, such as parallel to, aligned with, or in the same plane as, mean that the specified relationships are within limitations of manufacturing processes and within manufacturing variations. When components are described as being coupled, connected, being in contact or contacting one another, they need not be physically directly touching one another unless specifically described as such. Like elements in various embodiments are commonly referred to with like reference numerals.

An embodiment of an ablation system with improved refrigerant delivery area is shown in FIG. 1 and comprises an endoscope 1 and a cryogenic balloon ablation assembly 10. The endoscope 1 may be conventional and include an endoscopic tube 3 having proximal and distal ends 5, 7 defining a channel 8 extending between the proximal and distal ends.

Figure 2A:
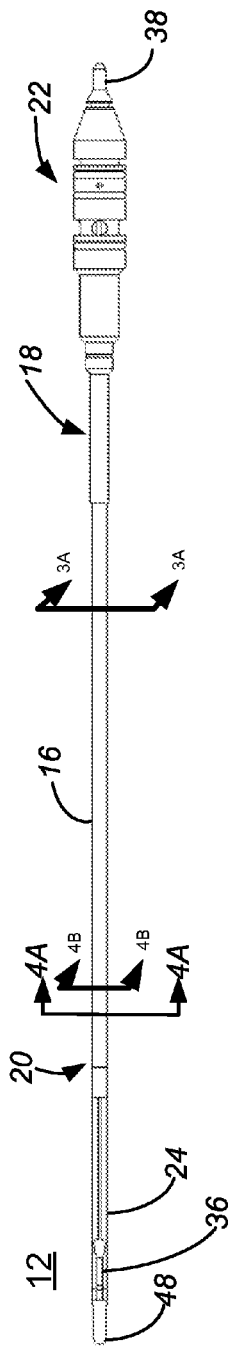
FIG. 2A illustrates an ablation catheter with a deflated balloon in tension.
Figure 2B:
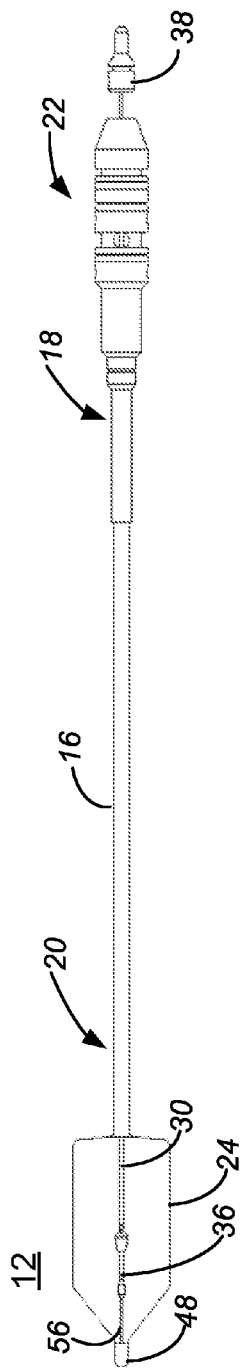
FIG. 2B illustrates an ablation catheter with an inflated balloon with the diffuser located in a middle region of the balloon.
Figure 2C:
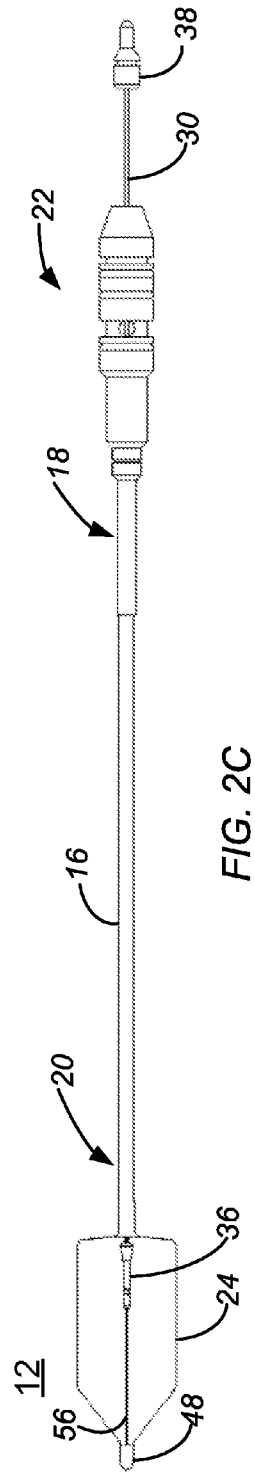
FIG. 2C illustrates an ablation catheter with an inflated balloon with the diffuser located in a proximal region of the balloon.

In embodiments, an ablation assembly 10 comprises a cryogenic ablation catheter 12 mounted to and extending from a handle assembly 14. FIGS. 2A, 2B and 2C show an embodiment of a cryogenic ablation catheter in three states that will be discussed below. Catheter 12 includes a catheter shaft 16 having a proximal end 18 and a distal end 20. At the proximal end 18 is a connector 22 to be received in the handle assembly 14. At the distal end 20 is a balloon 24 that is inflatable by a refrigerant delivered from a refrigerant fluid source in the handle assembly 14 to a diffuser 36 located within the balloon and fluidly coupled to a delivery tube 30. The diffuser 36 translates within the balloon along a rail 56 affixed to a flexible tip 48 at the distal end of the balloon 24, which is discussed in greater detail below. Translation of the diffuser 36 is caused by translation of a plug 38 affixed and fluidly coupled to the delivery tube 30 at the connector end of the catheter 12.

The catheter shaft 16 comprises a circular tube with a circular central lumen. The catheter shaft 16 may range from 120 cm to 200 cm in length and have an outer diameter ranging from 0.100" to 0.138". The proximal end of the catheter shaft 16 is affixed to the connector 22, and the distal end is affixed to the balloon 24.

Figure 3A:
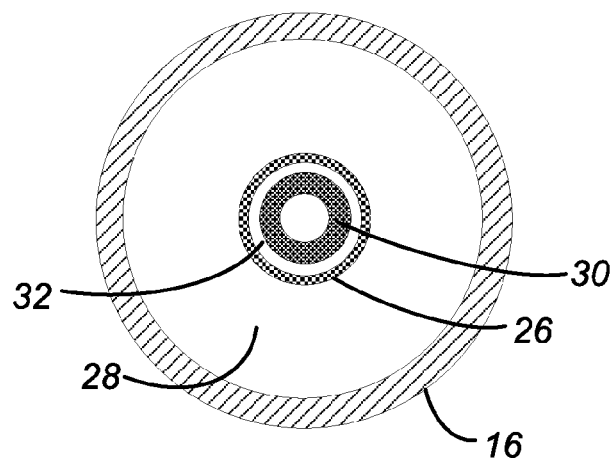
FIG. 3A is a cross-sectional view taken along line 3A-3A of FIG. 2A.

FIG. 3 shows cross-section 3A-3A of FIG. 2A. As shown, located within the catheter shaft 16 is a pressure detecting tube 26. The cavity between the inner wall of the catheter shaft and the outer wall of the pressure detecting tube defines an exhaust lumen 28 for the passage of gases from the balloon interior for discharge through the connector 22 and exhaust assembly 108, which will be discussed in greater detail below. The pressure detecting tube 26 includes a circular central lumen containing a delivery tube 30. The cavity between the inner wall of the pressure detecting tube 26 and the outer wall of the delivery tube 30 defines a pressure detecting lumen 32 used to detect the static pressure within the balloon 24.

Figure 4A:
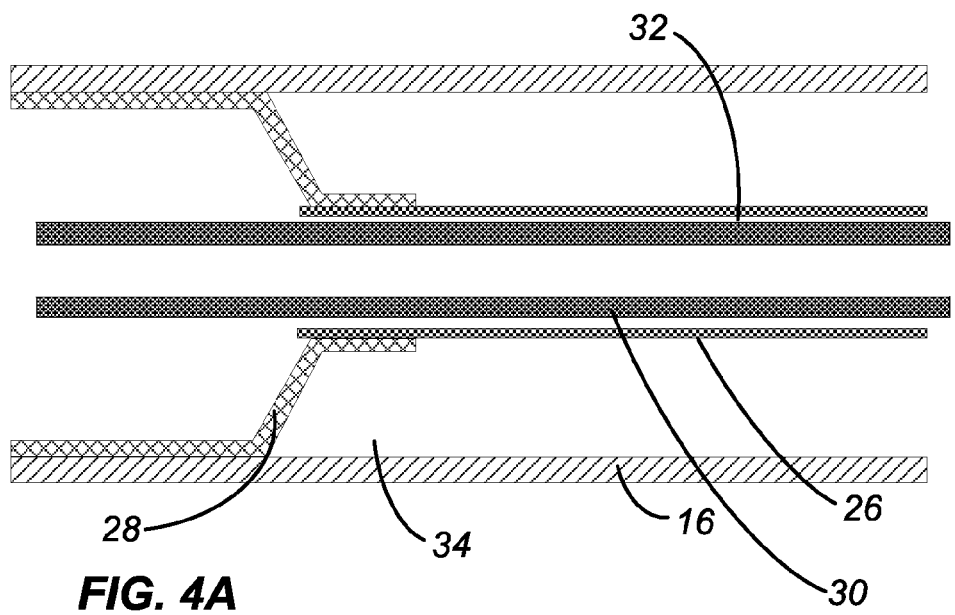
FIG. 4A is a cross-sectional view taken along line 4A-4A of FIG. 2A.
Figure 4B:
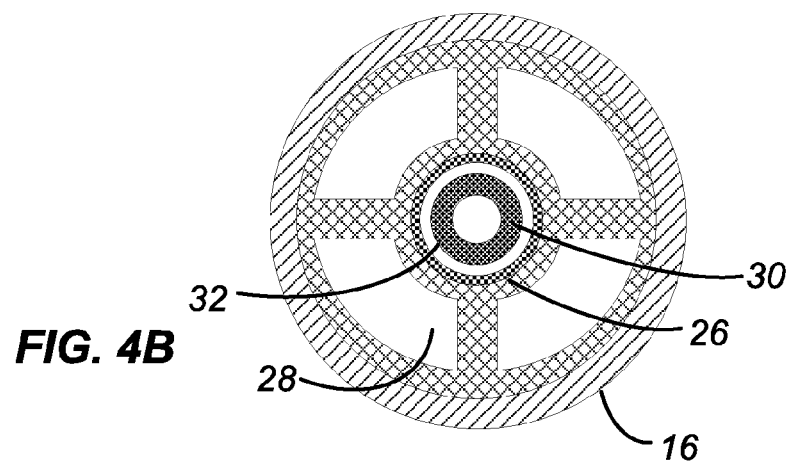
FIG. 4B is a cross-sectional view taken along line 4B-4B of FIG. 2A.

The pressure detecting tube 26 extends from near the balloon end of the catheter shaft 16 to the connector 22. The pressure detecting tube 26 is affixed to the catheter shaft 16 near the distal end 20 of the catheter shaft 16 to be concentric to the catheter shaft lumen. The affixing means includes a bracket 34 with minimal flow obstruction of the exhaust lumen as shown in FIGS. 4A and 4B. In embodiments. the bracket 34 is positioned a distance within the end of the catheter shaft 16 so that the a portion of the diffuser 36 may enter a portion of the catheter shaft 16 to allow delivery of refrigerant to portions of the balloon 24 located proximate to the distal end 20 of the catheter shaft 16.

As shown in FIG. 3, within the pressure detecting tube 26 is the delivery tube 30. The pressure detecting tube 26 is a guide for the delivery tube 30 ensuring consistent 1:1 translation of the delivery tube within the pressure detecting tube without backlash. For example when the plug end of the delivery tube 30 is translated 4 mm then the diffuser end is also translated 4 mm.

The delivery tube 30 extends from the plug 38 through the connector 22; through the pressure detecting tube 26, and to the diffuser 36. The delivery tube 30 is made of a strong flexible tubing or tubing assembly. For example, the delivery tube may be comprised of a tubing assembly including an outer nitinol tube, which is very elastic and does not plastically deform (e.g. kink) easily, and an inner thin-walled polyimide tube. The nitinol tubing provides structural support for the tubing assembly. The nitinol tubing provides the strength necessary to prevent buckling during axial translation of the delivery tube. Further, the nitinol tubing transmits torque well which allows for rotational movement of the delivery tube. In embodiments, the outer tube of a delivery tube assembly is a torque tube comprising stainless steel wires that undergo processes such as swaging, stretching, annealing, and then is wound around the inner tube to form a tubing assembly with good rotational and axial translation capabilities. The thin-walled polyimide inner tube is made with tight tolerances which allows for consist flow of refrigerant through the delivery tube. The delivery tube during use may experience internal pressures of 600 psi to 1200 psi and may be configured to have a wall thickness to withstand internal pressures up to 1500 psi. The delivery tube 30 translates within the pressure detecting tube 26 in response to movement of the plug 38 relative to the connector 22.

FIG. 2A shows a state of the plug 38, wherein the plug 38 abuts the connector 22 and the diffuser 36 is located at a position toward the distal end of the balloon 24, which is shown in a deflated state. FIG. 2B shows a state of the plug 38, wherein the plug 38 is located at a first intermediate position relative to the connector 22 and the diffuser 36 is located at a position in a middle region of the balloon 24, shown in an inflated state. FIG. 2C shows a state of the plug 38, wherein the plug 38 is located at a position toward the proximal end of the balloon 24

Figure 5A:
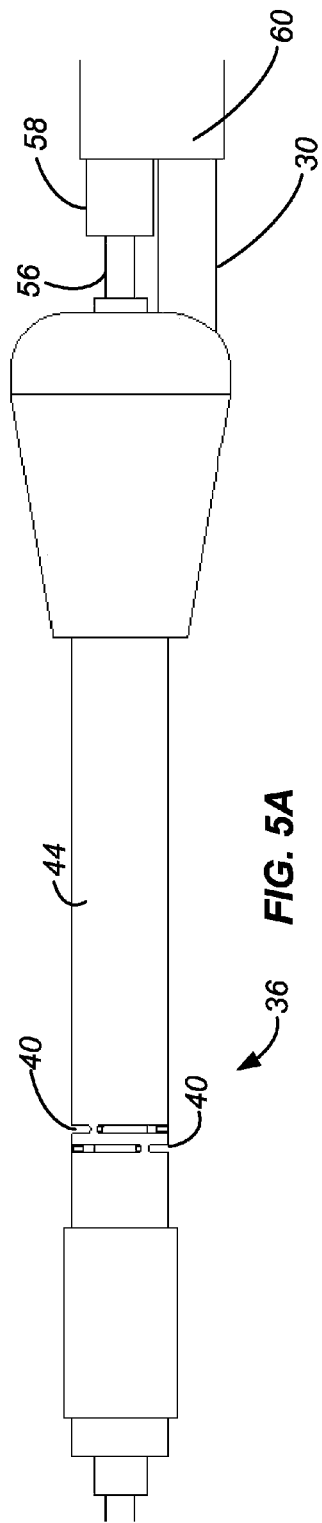
FIG. 5A illustrates an external view of the diffuser.
Figure 5B:
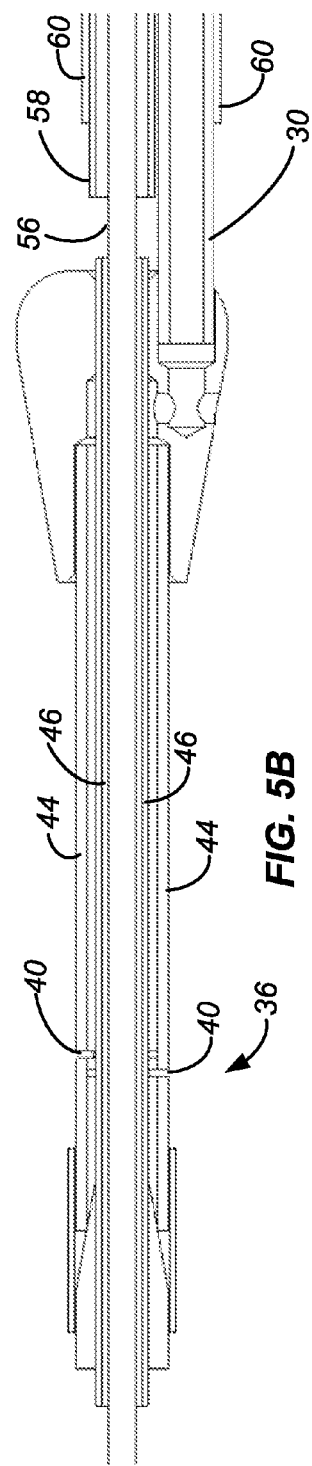
FIG. 5B is a cross section of the diffuser of FIG. 5A.
Figure 5C:
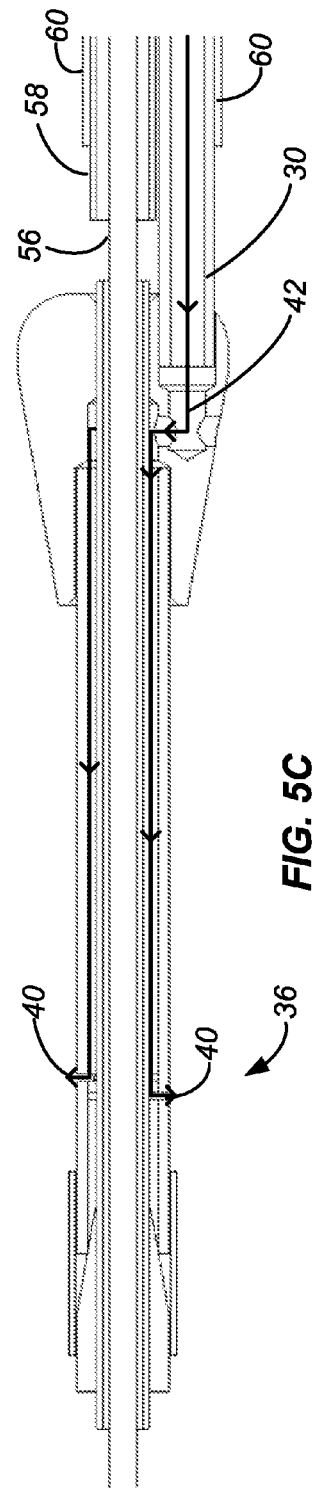
FIG. 5C is a cross section of the diffuser of FIG. 5A showing flow paths.

As shown in FIGS. 5A and 5B, the diffuser 36 is affixed to the distal end of the delivery tube 30. The diffuser 36 comprises a hollow internal cavity fluidly connected to the delivery tube 30 and the nozzle ports 40 which allow refrigerant supplied from a refrigerant fluid source in the handle assembly to be sprayed on the interior wall of the balloon 24. The path 42 of the refrigerant within the internal cavity is illustrated in FIG. 5C. The internal cavity includes a body cavity that is defined by the inner wall of the outer diffuser tube 44 and the outer wall of the inner diffuser tube 46. The nozzle ports 40 are formed through the wall of the outer diffuser tube 44. The nozzle ports 40 may be comprised of one or more slits located around the outer diffuser tube 44. The slits may be stacked in multiple rows to allow openings in the wall at all radial position, for example in embodiments where spray is to be delivered 360 degrees. In embodiments the desired delivery angle of the spray may be less than 360, for example 90 degrees or 180 degrees. In these embodiments the nozzle ports 40 will be sized and positioned to deliver the desired angle of spray. In embodiments the nozzle ports 40 includes slits 4 thousandths of an inch in height. The path 42, as shown in FIG. 5C, is configured to allow for even distribution of refrigerant by the point the refrigerant is at the nozzle port end of the diffuser 36 so that the pressure is equal radially around the inner cavity.

The balloon 24 is expandable and collapsible and is mounted to the distal end of the catheter shaft 16. FIG. 2A, shows a schematic of the balloon 24 in a deflated tension state, and FIGS. 2B and 2C, show the balloon 24 in an inflated state. Balloon 24 can be an elastic material, such as polyurethane, and can have an operating diameter in the range of 20 to 35 mm when inflated with less than 5 psi. Balloon 24 has an inner surface defining a balloon interior. In embodiments, the balloon 24 includes a tapered distal end secured to a flexible tip 48. During operation, refrigerant flows out through the nozzle ports 40 of the diffuser 36 generally radially outwardly to create refrigerant spray directed at a target site along the inner surface of the balloon 24. The target site of the inflated balloon is in contact with tissue and the delivery of refrigerant typically causes cryogenic ablation of tissue abutting target site of the balloon 24. In embodiments, the target site is larger than the area of spray delivery to the interior wall of the balloon 24 and the diffuser 36 translates along the length of the balloon 24 while spraying to deliver refrigerant to the entire target site. The portion of the balloon capable of receiving refrigerant spray and shaped to be capable of contacting tissue is referred to as the working length of the balloon. In embodiments, the working length of the balloon 24 includes straight wall portions, as shown in FIGS. 2B and 2C. The balloon may further include tapered wall portions that usually do not contact tissue or receive refrigerant spray, as shown in FIGS. 2B and 2C. In embodiments the balloon 24 may include strain gauges used as input into a controller 50, which is discussed in greater detail below.

The balloon 24 is shown in detail in FIGS. 6A, 6B, 6C and 6D. The flexible tip 48 is configured to assist in guiding the balloon end of the catheter while inserting the device into a device, such as an endoscope, or into a bodily passage, such as an esophagus. For example, endoscopes commonly have a kink in the port which the catheter is inserted. The flexible tip 48 is more flexible than the delivery tube 30 and prevents damage to the delivery tube 30 and balloon 24 during insertion of the catheter 12. For example, during initial insertion the flexible tip 48 may encounter an obstacle causing it to bend a substantial amount. This amount of bending may cause damage to the delivery tube 30 and render it inoperable. Therefore, the flexible tip 48 may act as a sacrificial bending point which may be caused to bend a large amount during initial insertion and not have an effect on the operability of the overall device because the delivery tube 30 will be able to pass by the obstacle with a more gentle bend because the flexible tip 48 is further along the path of insertion and able to guide the remainder of the catheter 12. Further, the flexible tip 48 may prevent damage to tissue in the body if during insertion the tip impacts tissue. As shown in FIG. 6B, the flexible tip 48 includes a rounded end 52 and a spring body portion 54. Affixed to the flexible tip 48 is a rail 56 that is used to position the diffuser 36 generally along a central axis of the balloon 24, and guide the diffuser 36 during translation within the balloon 24.

As shown in FIG. 6B, which depicts an inflated balloon 24 and omits the diffuser 36 and delivery tube 30 for ease of viewing the rail 56, the rail 56 extends from the flexible tip 48, through the balloon 24 and into the exhaust lumen 28. The rail 56 is not affixed to the interior of the exhaust lumen 28 and may move freely with the exhaust lumen 28. In embodiments, the rail is comprised of stainless steel, or other materials that have good properties including resistance to plastic deformation, even at colder temperatures.

The rail 56 is further located within the inner diffuser tube 46 and a guide 58, as shown in FIG. 6C. The guide 58 is affixed to the distal end of the delivery tube 30. The guide 58 may be a polyimide tube that is attached to the delivery tube 30 using a heat shrink material 60 around the guide and delivery tube. The guide 58 and the inner diffuser tube 46 are configured to be able translate along the length of the rail 56 so that the diffuser may translate from a point where the end of the diffuser contacts the flexible tip, as shown in FIG. 2A, to a point where the guide 58 is proximate or touching the pressure detecting tube 26 or bracket 34, as shown in FIG. 6D. Translating the delivery tube 30 toward the flexible tip 48 can cause the balloon 24 to stretch in the tension position shown in FIG. 2A, wherein the diffuser 36 contacts the flexible tip 48 causing it to translate further away from the catheter shaft 16, wherein the flexible tip 48 along with the rail 56 affixed to it are also caused to translate away from the catheter shaft 16 because at these position the diffuser 36 is no longer sliding along the rail 56. The uses and benefits of this stretched position will be discussed in detail below.

In embodiment the rail 56 may be a telescoping assembly comprised of multiple tube elements telescopically connected, wherein the diffuser is affixed to an end tube of the telescoping assembly. The telescoping element positions the diffuser in the center of the balloon similarly to the rail assembly disclosed above. In another embodiment, a rail may be affixed to the end of the diffuser and the balloon equipped with a long hollow tip portion to guide the rail on the end of the diffuser so the diffuser is in the center of the balloon.

Figure 7A:
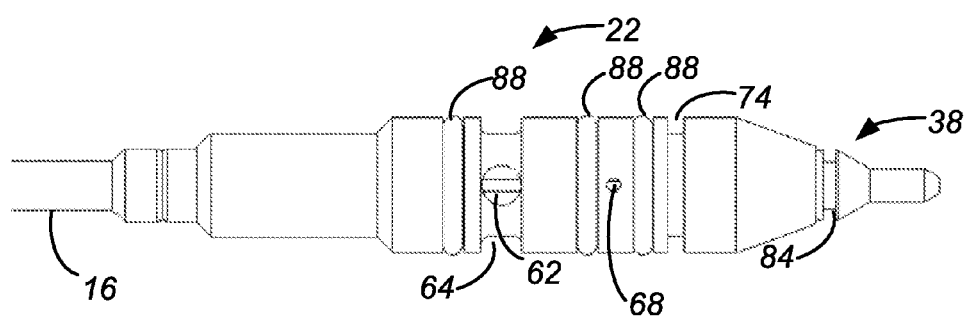
FIG. 7A illustrates an external view of the connector.
Figure 7B:
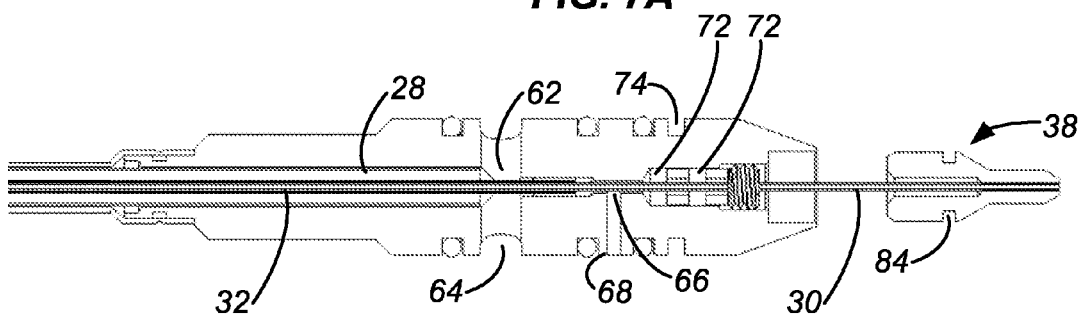
FIG. 7B is a cross section view of the connector of FIG. 7A.

FIG. 7A shows the connector 22. The proximal end of the catheter shaft 16 and the pressure detecting tube 26 are affixed to positions within the connector 22, as shown in FIG. 7B.

The connector 22 includes an exhaust passage 62 that fluidly couples the exhaust lumen 28 to a radial exhaust port 64 on the exterior of the connector 22. The connector 22 includes a pressure detecting passage 66 that fluidly couples the pressure detecting lumen 32 to a radial pressure detecting port 68 on the exterior of the connector 22. The connector 22 further includes a central passage 70 that the delivery tube 30 passes through between the pressure detecting passage 66 and the proximal end of the connecter 22, as shown in FIG. 7B. The delivery tube 30 is free to translate through the central lumen. The central passage 70 is separated from the pressure detecting passage 66 by one or more seals 72 that allow the delivery tube 30 to translate in the pressure detecting tube 26 and pressure detecting passage 66 but prevents gas from the pressure detecting passage 66 being leaked out the central passage 70.

Figure 8C:
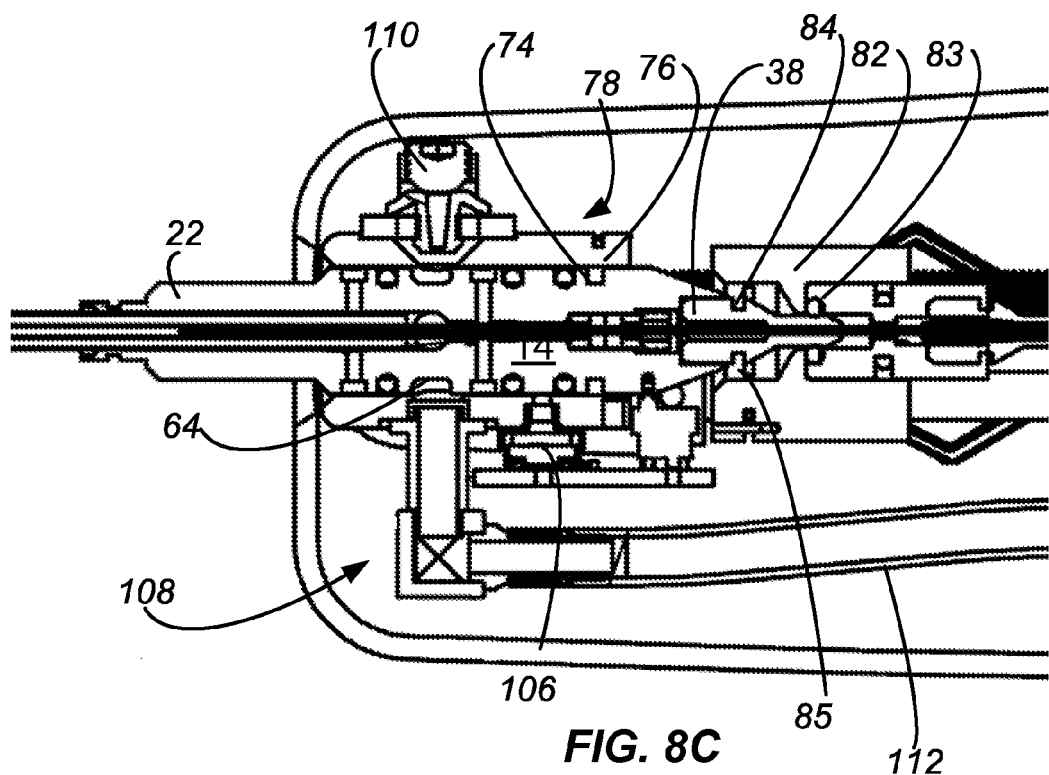
FIG. 8C is a detailed cross section view of a portion of the handle assembly with the connector attached.
Figure 8D:
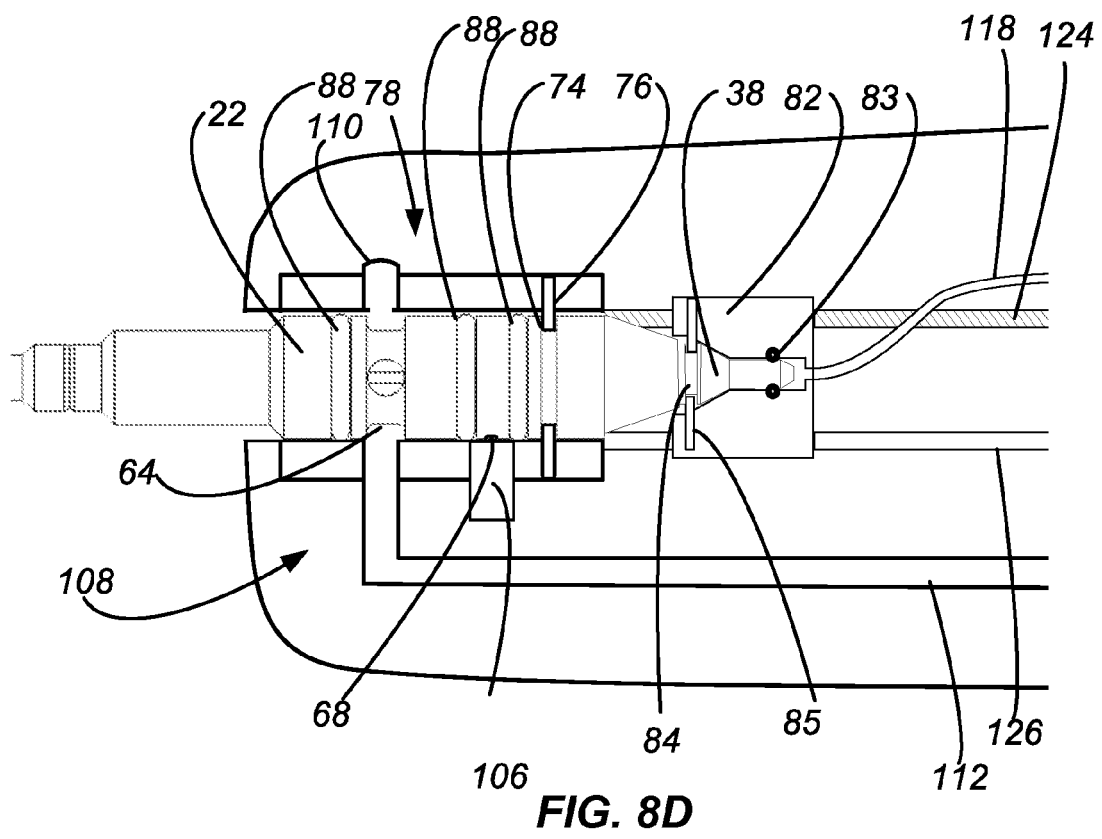
FIG. 8D is a simplified schematic cross section corresponding to FIG. 8C.

FIG. 8A shows a cross section of a handle assembly 14 prior to attaching the catheter 12, and FIG. 8B shows a simplified schematic cross section corresponding to FIG. 8A. To attach the catheter 12 to the handle assembly 14, as shown in FIG. 1, the plug end of the connector 22 is inserted into the opening 81 in the housing 80 and into a connector coupler 78 positioned adjacent to the opening in the housing 80. A receptacle lumen 86 of the connector coupler 78 forms a seal with the O-rings 88, shown in FIG. 7A, of the connector 22. The proximal end of the connector 22 includes an axial locking feature. In embodiments the axial locking feature is a circumferentially extending slot 74 that is engaged by a locking feature in the form of a retaining clip 76 in the connector coupler 78 of the handle assembly 14, as shown in FIG. 8C, and FIG. 8D which shows a simplified schematic cross section corresponding to FIG. 8C. Connector 22 is inserted through opening and into receptacle lumen 86 until the circumferentially extending slot 74 engages the one or more retaining clip 76. The handle assembly 14 further includes a plug coupler 82. A retaining clip 85 of the plug coupler 82 receives and lockingly engages a circumferentially extending slot 84 feature of the plug 38. The plug coupler 82 includes O-rings 83 which from a seal between the plug 38 and plug coupler 82 so that refrigerant delivered to the plug coupler is transmitted without leaks to the plug 38 and delivery tube 30.

As shown in FIGS. 8A and 8B, the handle assembly 14 further includes a handgrip portion 90 of the housing containing a power source in the form of a batteries 92, a forward portion 94 oriented generally perpendicular to handgrip 90, and a top portion 96 defining a threaded cylinder receptacle 98 for receipt of a refrigerant fluid source 100. Cylinder refrigerant fluid source 100 is secured within cylinder receptacle 98 using a threaded cap 99. In embodiments, a heater surrounding a portion of the cylinder receptacle is used to heat the contents of cylinder. Refrigerant is dispensed from cylinder gas source 100 in response to the initiation of a treatment by actuation of a trigger 104 coupled to the controller 50. Controller 50 will be discussed in more detail below.

Figure 7C:
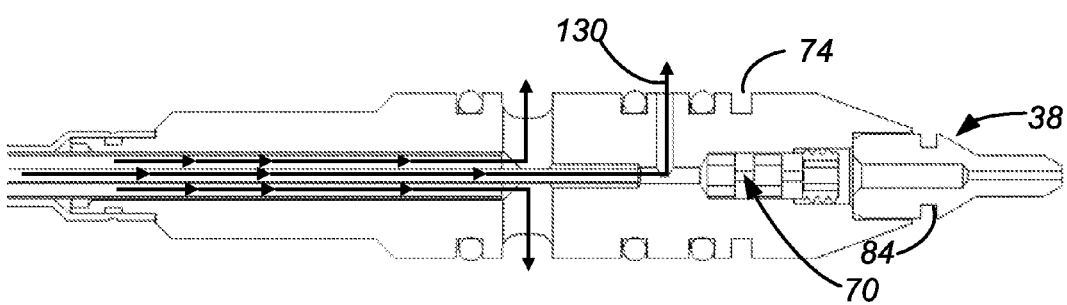
FIG. 7C is a cross section view of the diffuser of FIG. 7B omitting the delivery tube and showing flow paths.

The pressure within the balloon 24 is communicated to a pressure transducer 106 in the connector coupler 78. The pressure detecting lumen 32 is fluidly coupled to the pressure transducer 106 through the pressure detecting passage 66 and the pressure detection port 68. The fluid path 130 used to detect pressure is shown in FIG. 7C. The O-rings 88 on either side of the pressure detection port 68 form a seal within the connector coupler 78, as shown in FIG. 8D. Pressure transducer 106 is coupled to controller 50 to provide a pressure signal thereto. For clarity connection wires from components to the controller 50 are omitted from the figures.

Refrigerant delivered to the balloon 24 is exhausted through the exhaust lumen 28 to the exhaust radial exhaust port 64. If the pressure at the exhaust radial exhaust port 64 exceeds a threshold hold pressure a relief valve 110 exhausts the gas. Under normal operation conditions, exhaust gas from the radial exhaust port 64 flows through the connector coupler 78 and through an exhaust assembly 108. The exhaust assembly 108 includes exhaust tubing 112 and a controlled exhaust valve 114. In an embodiment, the controlled exhaust valve 114 is mechanically attached to the trigger 104 and depression of the trigger causes the controlled exhaust valve to open. In an embodiment, the controlled exhaust valve 114 may include an electronic actuator, for example a solenoid valve, wherein the electronic actuator controlled exhaust valve 114 is connected to and controlled by the controller.

Figure 8E:
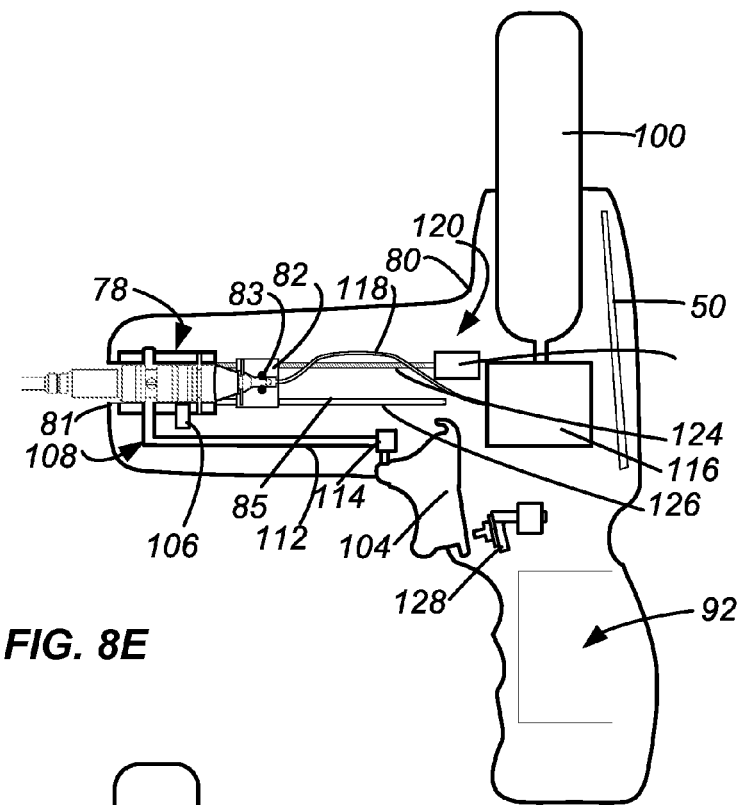
FIG. 8E is a simplified schematic cross section of the handle assembly with the plug coupler in a position corresponding to the plug position in FIG. 2A.
Figure 8F:
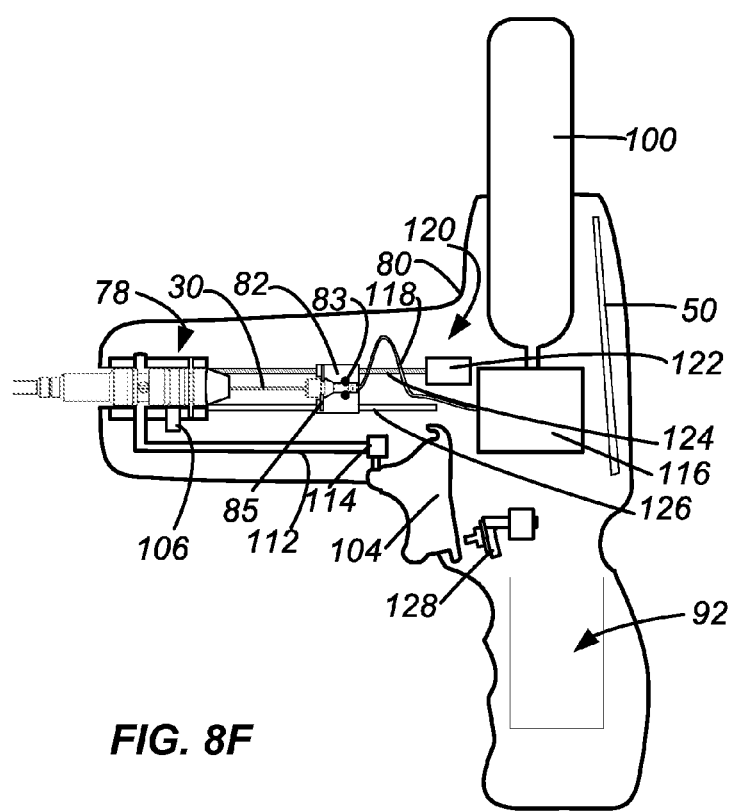
FIG. 8F is a simplified schematic cross section of the handle assembly with the plug coupler in a position corresponding to the plug position in FIG. 2C.

The handle assembly 14 further includes a flow control valve 116 and a connection line 118. The flow control valve 116 and a connection line 118 are fluidly coupled to the cylinder refrigerant fluid source 100 and the plug coupler 82, allowing refrigerant to be delivered through the delivery tube 30 to the diffuser 36. The flow control valve 116 controls the delivery of refrigerant from cylinder refrigerant fluid source 100 to the diffuser 36. In embodiments, the flow control valve is a solenoid valve that may be switched between an on position and an off position. The flow control valve 116 is coupled to the controller 50 and receives signals indicating the flow rate for a treatment. In embodiments, the controller 50 may send signals to the flow control valve 116 to abort refrigerant delivery based on system pressure. The connection line 118 is configured to have a shape that allows the connection line to be flexed and unflexed during translation of the plug coupler while maintaining a consistent fluid passage for refrigerant. For example, the connection line may be heat treated to have an initial shape curved shape. FIGS. 8E and 8F show schematics of the connection line 118 in a position when the plug coupler 82 is located toward and away from the connector coupler 78, respectively.

Translation of the plug coupler 82 causes translation of the delivery tube 30 and diffuser 36 within the balloon 24. A linear motion assembly 120 is connected to the plug coupler 82. In embodiments, the linear motion assembly 120 may cause the delivery tube 30 and diffuser 36 to translate at a rate between 0.25 mm/sec to 2.5 mm/sec, wherein the rate of translation for therapeutic use is between 0.5 mm/sec and 1.5 mm/sec. In embodiments, the linear motion assembly 120 includes a motor 122 coupled to a lead screw 124 and a track 126. The plug coupler 82 includes a threaded portion surrounding and engaged with the lead screw 124. The motor 122 rotates and causes the lead screw 124 to rotate. Rotation of the lead screw 124 causes translation of the plug coupler 82. In embodiments, the plug coupler further includes a track guide which engages with the track 126 so that the plug coupler 82 does not rotate when the lead screw rotates and is constrained to translate in the longitudinal direction of the lead screw 124. In embodiments, the linear motion assembly may include other forms of linear actuators including for example rack and pinion assemblies and belt assemblies.

Figure 9:
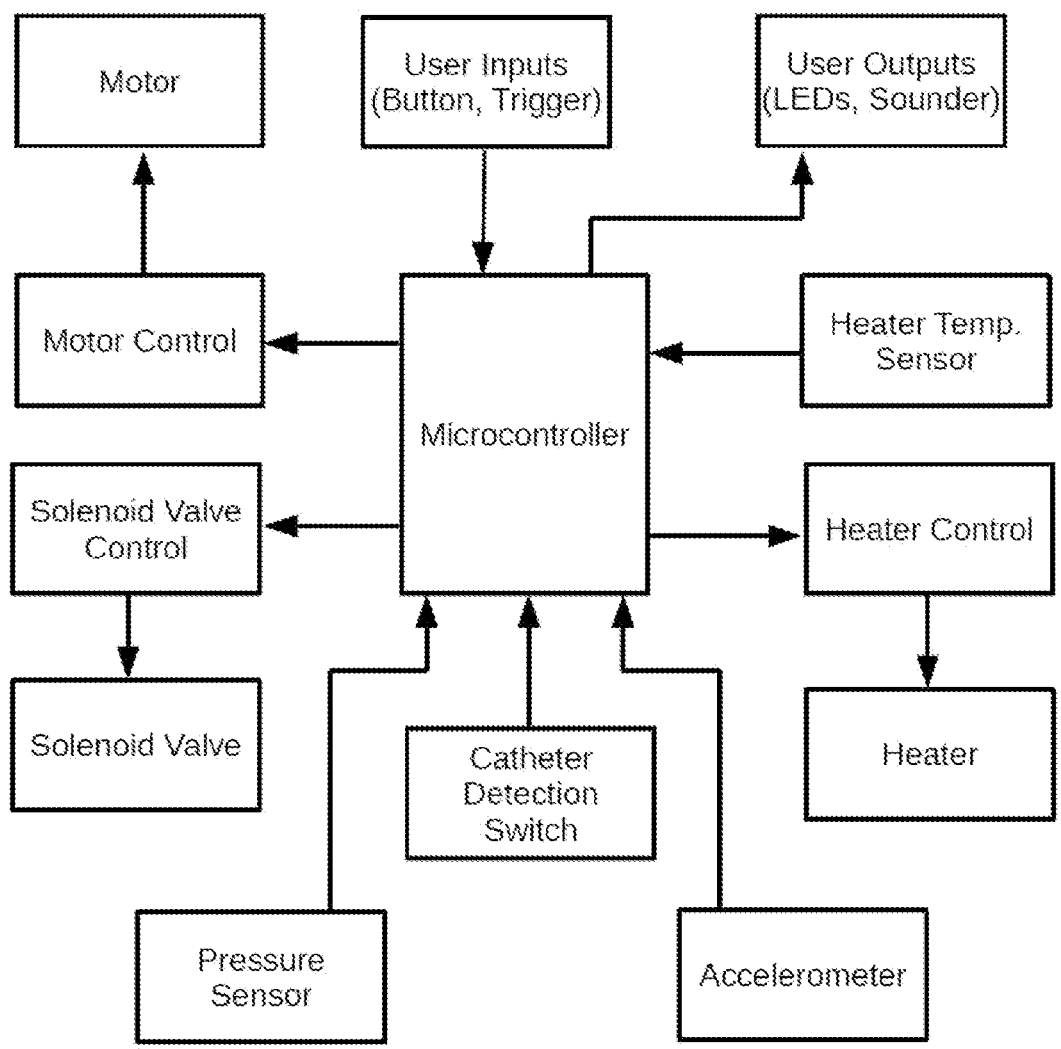
FIG. 9 is a simplified controller hardware architecture design chart.

The controller 50 may be used to control the delivery of refrigerant and translation of the delivery tube 30 and diffuser 36 within the balloon 24. The controller 50 includes circuitry connected to the flow control valve 116, linear motion assembly 120 and pressure transducer 106 described above. To initiate a treatment, a user may depress the trigger 104 which in turn depresses a button 128 connected to the controller 50. In embodiments, during release of refrigerant into the balloon 24 the controller 50 generates a pressure response curve from pressure date from the pressure transducer 106, which correlates to the inner diameter of the lumen to be treated. The controller 50 uses a pressure algorithm to determine the rate of speed for the linear actuator appropriate for treatment. In embodiments, a strain gauge or gauges on the balloon 24 may be used by the controller 50 to derive balloon diameter which corresponds to the inner diameter of the treated lumen. In embodiments the controller may be attached to other forms of user interfaces including buttons on the housing of the handle assembly, foot switches and touch displays. FIG. 9 is a simplified diagram showing the basic organization of control electronics of the controller 50. In embodiments, the control electronics may be connected to additional components including user outputs including lights and displays, temperature sensors, heater controllers, accelerometers, detector switches, and solenoid valves. The controller may contain treatment algorithms and the inputs of components may be used by the algorithms to adjust treatment parameters, for example duration, flow rate of refrigerant, translation distance, and translation speed.

In embodiments, the catheter may include an RFID tag identifying properties of the catheter including size of balloon, angle of spray of diffuser. The controller in the handle may receive this info from an RFID reader in the handle assembly and input the information into a treatment algorithm in order to adjust treatment parameters depending on the properties of the attached catheter. The RFID may be used for authentication purposes. For example, a non-conforming catheter (e.g. reused or overused catheter, or catheter made by an uncertified manufacturer) may be detected by the controller and the controller will lock out the device from operating with the non-conforming catheter attached. The RFID may further be used for orientation purposes to ensure catheter is oriented properly.

In embodiments, the user may select a treatment algorithm prior to initiating the treatment. Additionally the user may be able to input various parameters to be used in the selected treatment algorithm. The information may include patient data, catheter information and number of treatments performed. The user interface for selecting and setting a treatment may include a display or touch display on the handle assembly, an array of lights, or may be programmed remotely and receive by the controller wirelessly, wired or via a removable memory card.

The controller may record the number of uses of a catheter and save this information, or transmit this information to a central database to ensure no overuse of catheters. In embodiments, RFID tags on the catheter may be writeable so the controller can program catheter to be read in the future. The written material may include a lockout or a time of last use.

The following is an example procedure of an ablation procedure. An endoscope is inserted in the esophagus of a patient. Ablation catheter 12 with the plug 38 in the most distal position as shown in FIG. 2A is inserted into the proximal end 5 of the channel 8 of endoscopic tube 3. The plug 38 in the most distal position causes the diffuser 36 to push the flexible tip 48 away from the catheter shaft 16 causing the deflated balloon 24 to be in tension. The catheter 12 is inserted through the channel 8 until the balloon 24 exits the distal end 7. Using the monitor attached to the endoscope the user is able to see the balloon exit. The catheter 12 is placed into an initial desired position and the handle assembly 14 is attached as described above.

The user selects a treatment algorithm, inputs any necessary parameters, and depresses the trigger in order to initially inflate the balloon 24. This initial inflation is required to visualize the location of target site relative to the lesion to be ablated. This initial inflation may include translating the diffuser to a position to allow for the balloon to be relaxed and no longer in tension. An example of this position is shown in FIG. 2B. This is followed by a short burst of refrigerant spray delivered onto inner surface of balloon 24 which inflates the balloon and allows the user to visually determine the location of the target site using the endoscope because of the freezing which occurs at tissue near the target site. If necessary, ablation assembly can be repositioned axially; this may or may not require the partial deflation balloon 24 followed by re-inflation of the balloon. In embodiments with a directional spray as opposed to 360 degrees, during repositioning the catheter assembly may be rotated to cause the nozzle ports 40 to rotate. In embodiments the assembly may have the ability to rotate the delivery tube and diffuser to reposition the radial direction of refrigerant spray.

Once balloon 24 is properly positioned and inflated so that the nozzle ports 40 are directed at a portion of the lesion or other tissue to be cryogenically treated at the most distal end of the balloon, refrigerant is delivered to the diffuser to be sprayed on the interior wall of the balloon 24. While the refrigerant is being sprayed the diffuser translated toward the proximal end of the balloon. The flow rate of refrigerant and translation rate of the diffuser are ideally set so that an ideal amount of refrigeration energy is received by each portion of the lesion to ensure ablation of the entire desired area. In the occurrence that the translation of the delivery tube assembly jams for any reason, the controller will stop the delivery of refrigerant to prevent over ablation of tissue that may cause damage.

Due to the direction of exhaust, it is beneficial to begin ablation from the distal end of the balloon as disclosed above because cool exhaust gas will pass over portions of the balloon interior surface that will subsequently be sprayed by refrigerant. This flow of exhaust gas therefore has a pre cooling effect which reduces the temperature prior to delivery which allows for less refrigerant to be used in order to achieve a desired ablation temperature. This pre-cooling effect is factored into the treatment algorithms.

The above descriptions may have used terms such as proximal, distal, above, below, top, bottom, over, under, et cetera. These terms may be used in the description and claims to aid understanding of the invention and not used in a limiting sense.

While the present invention is disclosed by reference to the preferred embodiments and examples detailed above, it is to be understood that these examples are intended in an illustrative rather than in a limiting sense. It is contemplated that modifications and combinations will occur to those skilled in the art, which modifications and combinations will be within the spirit of the invention and the scope of the following claims.

What is claimed is:

1. A cryogenic balloon ablation assembly comprising:
    a cryogenic ablation catheter comprising:
        a catheter shaft having proximal and distal ends and a catheter shaft lumen extending between the proximal and distal ends;
        an expandable and collapsible balloon mounted to the distal end of the catheter shaft, the balloon having an inner surface defining a balloon interior;
        a delivery tube assembly comprising:
            a delivery tube housed within the catheter shaft for axial movement relative to the catheter shaft; and
            a diffuser, within the balloon, fluidly coupled to the delivery tube; and
        a pressure detecting tube fluidly coupled to a pressure detecting transducer, wherein the delivery tube is configured to translate axially within the pressure detecting tube; and a handle assembly comprising:
   a refrigerant fluid source fluidly coupled to the delivery tube assembly,
wherein the diffuser is configured to translate axially within the balloon while an outlet of the diffuser directs refrigerant from the refrigerant fluid source outwardly towards the inner surface of the balloon.

2. The cryogenic balloon ablation assembly of claim 1:
the cryogenic ablation catheter further comprising:
   a connector at the proximal end of the catheter shaft; and
   the delivery tube assembly further comprising a plug proximate to the connector and fluidly coupled to the delivery tube and refrigerant fluid source,
   wherein translation of the plug relative to the connector causes the axial movement of the diffuser within the balloon.

3. The cryogenic balloon ablation assembly of claim 2, further comprising:
a linear actuator within the handle assembly configured to translate the delivery tube axially through the connector.

4. The cryogenic balloon ablation assembly of claim 3, further comprising:
a controller;
wherein the controller is configured to control a flow control valve fluidly in line between the refrigerant fluid source and the diffuser; and
wherein the controller is configured to control the linear actuator.

5. The cryogenic balloon ablation assembly of claim 4, wherein the controller is configured to use input received from the pressure transducer, detecting pressure within the balloon, to abort treatment if abnormal pressures are detected.

6. The cryogenic balloon ablation assembly of claim 5, wherein the controller is configured to use a diameter of the balloon in an inflated state to determine a rate of speed of the linear actuator.

7. The cryogenic balloon ablation assembly of claim 4, wherein the controller is configured to receive input from the pressure transducer, detecting pressure within the balloon, to determine a diameter of the balloon in an inflated state.

8. The cryogenic balloon ablation assembly of claim 4, wherein the controller determines a rate of speed of the linear actuator using information received about the cryogenic ablation catheter.

9. The cryogenic balloon ablation assembly of claim 8, wherein the information received about the cryogenic ablation catheter is received from an RFID tag reader in the housing handle assembly configured to read an RFID tag on the cryogenic ablation catheter.

10. The cryogenic balloon ablation assembly of claim 1, further comprising:
a rail with a first end affixed to a tip portion of the balloon and a second end within the catheter shaft;
wherein the diffuser is configured to translate axially along the rail.

11. A cryogenic balloon ablation assembly comprising:
a cryogenic ablation catheter comprising:
   a catheter shaft having proximal and distal ends and a catheter shaft lumen extending between the proximal and distal ends;
   an expandable and collapsible balloon mounted to the distal end of the catheter shaft, the balloon having an inner surface defining a balloon interior; and
   a delivery tube assembly comprising:
      a delivery tube housed within the catheter shaft for axial movement relative to the catheter shaft; and
      a diffuser, within the balloon, fluidly coupled to the delivery tube; and
a handle assembly comprising:
   a refrigerant fluid source fluidly coupled to the delivery tube assembly;
   a linear actuator configured to translate the delivery tube axially through a connector at the proximal end of the catheter shaft; and
   a controller configured to control a flow control valve fluidly in line between the refrigerant fluid source and the diffuser, and further configured to control the linear actuator;
wherein the diffuser is configured to translate axially within the balloon while an outlet of the diffuser directs refrigerant from the refrigerant fluid source outwardly towards the inner surface of the balloon; and
wherein the controller is configured to use a diameter of the balloon in an inflated state to determine a rate of speed of the linear actuator.

* * * * *